(12) United States Patent
Taylor

(10) Patent No.: US 6,626,944 B1
(45) Date of Patent: *Sep. 30, 2003

(54) INTERSPINOUS PROSTHESIS

(76) Inventor: Jean Taylor, 141 rue d'Antibes, 06400 Cannes (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/622,513

(22) PCT Filed: Feb. 19, 1999

(86) PCT No.: PCT/FR99/00383

§ 371 (c)(1),
(2), (4) Date: Oct. 23, 2000

(87) PCT Pub. No.: WO99/42051

PCT Pub. Date: Aug. 26, 1999

(30) Foreign Application Priority Data

Feb. 20, 1998 (FR) .............................. 98 02300

(51) Int. Cl.$^7$ ............................ A61F 2/44; A61B 17/70
(52) U.S. Cl. ................................ 623/17.16; 623/17.11; 606/61
(58) Field of Search .......................... 623/17.11, 17.16; 606/61; A61B 17/56, 17/70; A61F 2/44

(56) References Cited

U.S. PATENT DOCUMENTS

| 4,570,618 | A | | 2/1986 | Wu | |
|---|---|---|---|---|---|
| 5,011,484 | A | * | 4/1991 | Breard | ..................... 623/17.16 |
| 5,496,318 | A | * | 3/1996 | Howland et al. | .............. 606/61 |
| 5,609,634 | A | * | 3/1997 | Voydeville | ................... 623/17 |
| 5,645,599 | A | * | 7/1997 | Samani | ..................... 623/17.16 |

FOREIGN PATENT DOCUMENTS

| DE | 31 13 142 C2 | | 5/1985 | |
|---|---|---|---|---|
| EP | 0 322 334 A1 | | 6/1989 | |
| EP | 1 138 268 A1 | * | 10/2001 | ........... A61B/17/70 |
| FR | 2 623 085 A1 | | 5/1989 | |
| FR | 2 717 675 A1 | | 9/1995 | |
| FR | 2 730 156 A1 | | 8/1996 | |
| FR | 2 816 197 A1 | * | 5/2002 | ........... A61B/17/70 |
| WO | WO 01/28442 A1 | * | 4/2001 | ........... A61B/17/70 |
| WO | WO 02/03882 A2 | * | 1/2002 | ............. A61F/2/44 |

* cited by examiner

*Primary Examiner*—Corrine McDermott
*Assistant Examiner*—Javier S. Blanco
(74) *Attorney, Agent, or Firm*—Cantor Colburn LLP

(57) ABSTRACT

This prosthesis is made of a material which is multdirectionally flexible and elastic, and comprises an interspinous portion having a thickness slightly greater than the anatomical interspinous space when the spine is in lordosis. According to the invention, the prosthesis has two pairs of lugs projecting longitudinally on either side of its interspinous portion, these lugs having substantial heights in relation to the total height of the prosthesis, namely, for each pair of lugs, of the order of 30 to 45% of this total height; each pair of lugs is integral with the said interspinous portion and delimits a deep recess which is able to receive the corresponding spinous apophysis without play, with a wide surface area of contact between these lugs and this apophysis.

12 Claims, 2 Drawing Sheets

INTERSPINOUS PROSTHESIS

TECHNICAL FIELD

The present invention relates to an interspinous prosthesis intended to provide disc support and to dampen the relative movements of two adjacent vertebrae during the flexion or extension movements of the spinal column.

BACKGROUND OF THE INVENTION

French Patent No. 94. 03716, filed in the name of the Applicant, describes a prosthesis comprising a body made of flexible material and two rigid, V-shaped inserts. The body is intended to be inserted between the spinous apophyses of two vertebrae in order to maintain a flexible anatomical spacing between them, while at the same time permitting their relative movement. The inserts make it possible to delimit grooves for receiving the spinous apophyses of the two vertebrae and they comprise a means for fixing the prosthesis to these apophyses.

The prosthesis according to said earlier patent is satisfactory in practice, but it has become evident that it could be improved, particularly as regards its structure and its resistance to the repeated stresses to which it is subjected. This is because the joins between the body of the prosthesis and the inserts are the focus of considerable stressing.

French Patent Application No. 2,623,085 describes an H-shaped wedge structure which has, on only one of its two end faces, or on both, a groove which is dimensioned to receive, with slight lateral play, a respective spinous apophysis. Each groove is delimited by lips of small height which, viewed from the side, have the shape of an arc of a circle.

The object of the present invention is to make available an interspinous prosthesis ensuring perfect support of the two vertebrae concerned, and consequently permitting perfect disc support, which prosthesis has to be able to resist the repeated stresses exerted on it by the apophyses, has to be designed so as to undergo only minimal wear, and has to exhibit considerable stability in all directions, in particular with respect to "lateral tilt" movements, that is to say movements provoked by torsion of the spine on its axis.

SUMMARY OF THE INVENTION

The prosthesis which is the subject-matter of the present patent application is, in a manner known per se, made of a material which is multi-directionally flexible and elastic, and comprises an interspinous portion having a thickness slightly greater than the anatomical interspinous space when the spine is in lordosis, such that this portion is compressed slightly when the prosthesis is placed between the spinous apophyses of two vertebrae.

According to the invention, the prosthesis has two pairs of lugs projecting longitudinally on either side of its interspinous portion, these lugs having substantial heights in relation to the total height of the prosthesis, namely, for each pair of lugs, of the order of 30 to 45% of this total height, each pair of lugs being integral with the said interspinous portion and delimiting a deep recess which is able to receive the corresponding spinous apophysis without play, with a wide surface area of contact between these lugs and this apophysis.

These deep recesses ensure that the prosthesis is held perfectly in position between the spinous apophyses of the vertebrae, in all directions, and in particular with respect to movements resulting from torsion of the spine on its axis, which movements tend to create a lateral tilting of the prosthesis.

Moreover, and in partiuclar, the combination of this structure of multi-directionally flexible and elastic material, on the one hand, and of these two pairs of lugs of substantial length forming a unit with the interspinous portion of the prosthesis, on the other hand, means that when this interspinous portion is under compression, the lugs can be made to bear against the lateral faces of the spinous apophyses, by means of a "self-closing" effect.

This holding of the prosthesis, allied with the flexibility of this prosthesis, permits substantial reduction in the friction between the prosthesis and the apophyses, which renders unnecessary the inserts of rigid material in the prosthesis according to the prior art. The prosthesis according to the invention is thus monobloc, which also solves the problems associated with manufacture, and especially with the strength of the prosthesis according to the prior art over the course of time.

The prosthesis according to the invention combines an effect of suppressing the contacts newly created between the facets following intense bearing, and an effect of reducing the intradiscal pressure, permitting a slowing down in the ageing of the disc.

The main indications for this prosthesis are:
arthropathy of the facets;
prevention of disc degeneration occurring subsequent to arthrodesis;
"relief" of the disc ring remaining after surgical treatment of a herniated disc.

The internal faces of two lugs of one and the same pair of lugs are preferably inclined in such a way as to converge towards one another in the direction of the bottom of the recess which they delimit.

A relative wedging of the apophysis is thus obtained by slight elastic deformation of the lugs, which contributes to holding the prosthesis in relation to the apophyses.

The lugs advantageously have an average thickness which is relatively great in relation to the average width of the prosthesis, namely, for each lug, of the order of 25 to 35% of this average width.

These lugs are thus perfectly integral with the interspinous portion of the prosthesis, which ensures their resistance to the repeated stresses to which the latter is subjected.

Preferably, the anterior face of the prosthesis connects respectively with the upper and lower faces of the prosthesis via slanted and/or rounded zones, permitting the total absence of the angles which these pairs of faces would otherwise form.

The prosthesis can thus be placed in the area of the base of the spinous apophyses, at the lamina/spinous process junction of the vertebrae, which reduces the extent of the torsional stresses which the apophyses are capable of exerting upon it.

The prosthesis is advantageously bored with at least one transverse conduit formed in the area of its interspinous portion, this conduit permitting the engagement of a cord intended to join the prosthesis tightly to at least one of the spinous apophyses.

These cords are simply intended to secure the positioning of the prosthesis, the latter being self-closed between the apophyses as a result of its aforementioned structure.

Preferably, the wall of the interspinous portion which delimits this conduit is widened at the ends of this conduit, in order to eliminate any sharp edge capable of creating a point of wear of the said cord.

According to a preferred embodiment of the invention in this case, the prosthesis comprises two transverse conduits, each receiving a cord for connecting it to the spinous apophysis of the corresponding vertebra.

The prosthesis according to the invention is advantageously placed in a textile sheath which matches its shape.

This sheath avoids direct contact between the synthetic material from which it is made, in particular silicone, and the surrounding tissues, and it facilitates the incorporation of the prosthesis with these tissues. In addition, it constitutes a means of limiting the stretching of the prosthesis, eliminating any risk of the latter breaking under exceptionally high loads.

This sheath advantageously comprises a small strip sewn onto it on the posterior side of the prosthesis, which can serve as an anchoring point for a prosthetic ligament replacing the interspinous and supraspinous ligament.

BRIEF DESCRIPTION OF THE DRAWINGS

To ensure that the invention is clearly understood, it is again described hereinbelow with reference to the attached diagrammatic drawing which represents, by way of a non-limiting example, a preferred embodiment of the interspinous prosthesis to which the invention relates.

DETAILED DESCRIPTION OF THE PREFERRED EMBODIMENT

Figure 1:
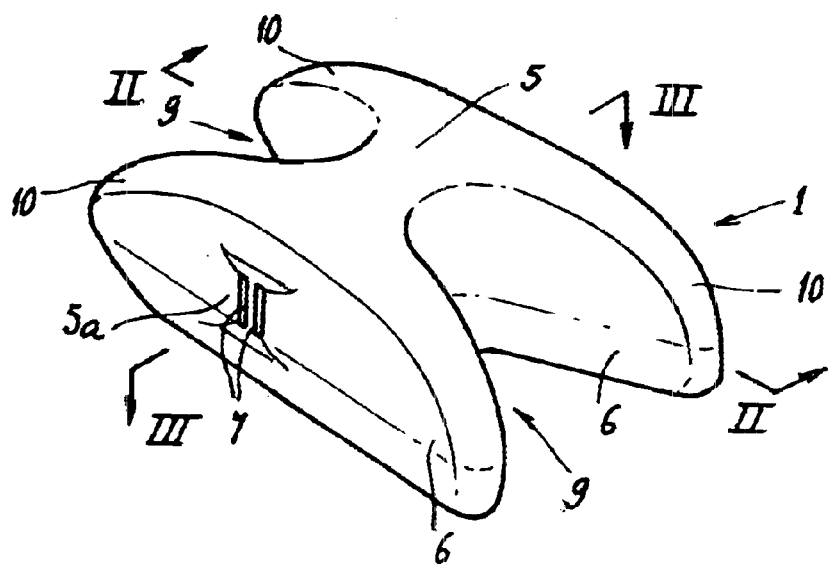
FIG. 1 is a perspective view of a silicone component which this prosthesis comprises.
Figure 2:
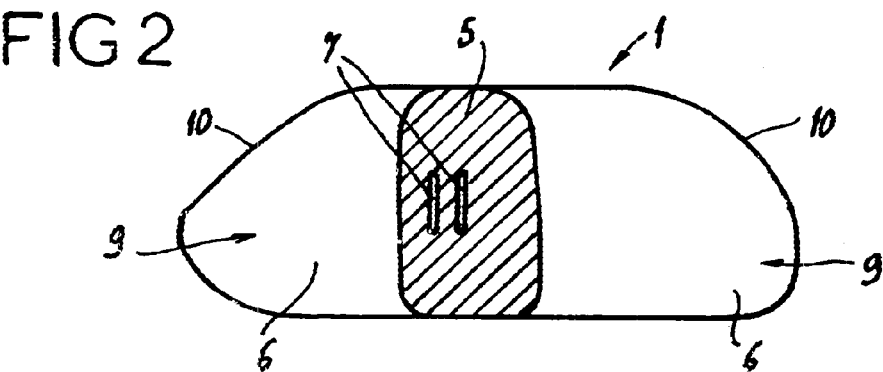
FIGS. 2 and 3 are cross-sectional views of this component along the lines II—II and III—III, respectively, in FIG. 1, and FIGS. 4 and 5 are perspective views of the prosthesis during two phases of implantation on vertebrae.
Figure 3:
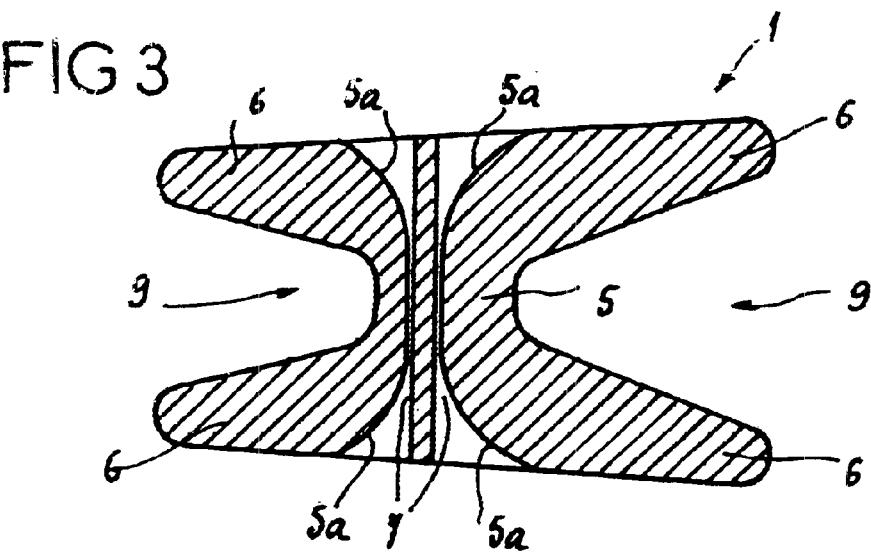
Figure 4:
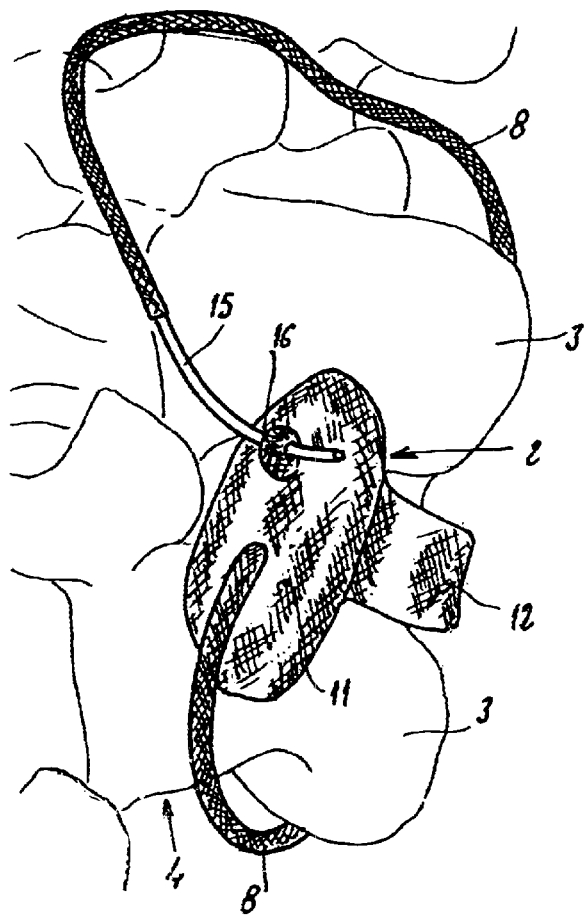
Figure 5:
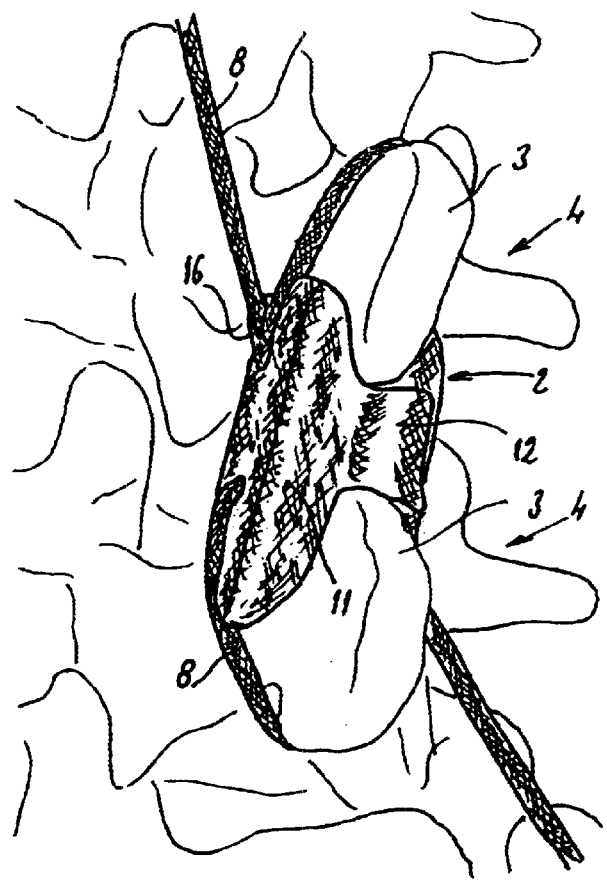

FIGS. 1 to 3 show, at different angles, a silicone component 1 constituting the core of an interspinous prosthesis 2. As can be seen in FIGS. 4 and 5, this prosthesis 2 is intended to be placed between the spinous apophyses 3 of two adjacent vertebrae 4 in order to dampen the relative movements of these vertebrae 4 during movements of flexion and extension of the spinal column.

The component 1 comprises an interspinous portion 5 and two pairs of lateral lugs 6 projecting longitudinally on either side of this portion 5.

The portion 5 has a thickness slightly greater than the anatomical interspinous space when the spine is in lordosis; it is thus compressed slightly when the prosthesis 2 is placed between the apophyses 3.

This portion 5 is bored with two transverse conduits 7 which, as is shown in FIGS. 4 and 5, permit the engagement of two cords 8 which serve to join the prosthesis 2 tightly to each of the apophyses 3. The wall 5a of the portion 5 which delimits each of these conduits 7 on the side of the corresponding lugs 6 is widened at the ends of the conduit 7 in order to eliminate any sharp edge which might create a point of wear of the cord 8.

The lugs 6 have substantial heights compared to the total height of the prosthesis 2, namely, for the upper and lower lugs, of the order of 33% and 40% of this total height, respectively.

The internal faces of two lugs 6 of one and the same pair of lugs are inclined in such a way as to converge towards one another in the direction of the bottom of the recess 9 which they delimit between them; in the example shown in the drawing, the angle formed by the two walls of the upper lugs is of the order of 27°, while the angle formed by the two walls of the lower lugs is of the order of 43°.

The lugs 6 additionally have an average thickness which is relatively great compared to the average width of the prosthesis 2, namely, for the upper and lower lugs, of the order of 27% and 30% of this average width, respectively.

It will also be seen in FIGS. 1 and 2 that the anterior face of the component 1 connects respectively with the upper and lower faces thereof via zones 10 which are slanted or rounded, permitting the total absence of the angles which would otherwise be formed by these anterior and upper or lower faces.

The component 1 is placed in a textile sheath 11, made of polyester, which matches its shape and which is bored with holes arranged in line with the openings of the conduits 7.

This sheath 11 comprises a small strip 12 sewn onto it on the posterior side of the prosthesis 2, intended to serve as an anchoring point for a prosthetic ligament replacing the intraspinous and supraspinous ligament.

It will be seen from FIGS. 4 and 5 that each cord 8 consists of a braid, one end of which is crimped onto the end of a curved needle 15, and the other end of which includes a ring 16.

In practice, the prosthesis 2 is inserted into the interspinous space intended to receive it. By virtue of its zones 10, it can be inserted into the bottom of this space, as far as the junction of the laminae and the spinous processes of the vertebrae 4.

Each cord 8 is introduced into the conduit 7 corresponding to it, then engaged, by means of the needle 15, around the corresponding spinous apophysis 3, and then through the ring 16. After suitable tensioning of the cord 8, a limit stop component (not shown), comprising a stop flange and a sleeve tube capable of being crimped around the cord 8, is engaged on this cord 8 until the said flange bears against the ring 16. The said sleeve tube is then crimped onto the cord 8 in order to fix this cord, and the free, unused end of the cord 8 is cut flush with this sleeve tube.

It goes without saying that the invention is not limited to the embodiment which has been described above by way of example, but that, on the contrary, it encompasses all the alternative embodiments. Thus, the component 1 could be used on its own, without the sheath 11, this component 1 then itself constituting the prosthesis according to the invention.

What is claimed is:

1. Interspinous prosthesis, comprising:
   an interspinous portion having a thickness slightly greater than the anatomical interspinous space when the spine is in lordosis, such that the interspinous portion is compressed slightly when the prosthesis is placed between the spinous apophyses of two vertebrae, and
   two pairs of lugs projecting longitudinally on either side of the interspinous portion;
   wherein, the interspinous prosthesis is composed of a multi-directionally flexible and elastic material, each pair of lugs is integral with the interspinous portion and delimits a deep recess for receiving the corresponding spinous apophysis with a wide surface area of contact between the lugs and the apophysis, and the two pairs of lugs have a length substantially larger than a length of the interspinous portion such that the lugs bear against the spinous apophyses when the interspinous portion is compressed.

2. Prosthesis according to claim 1, wherein the internal faces of two lugs of one and the same pair of lugs are inclined in such a way as to converge towards one another in the direction of the bottom of the recess which they delimit.

3. Prosthesis according to claim 1, wherein the lugs have an average thickness of 25 to 35% of the average width of the prosthesis.

4. Prosthesis according to claim 1, wherein an anterior face of the prosthesis includes a slanted and rounded zone.

5. Prothesis according to claim 1, further including at least one transverse conduit formed in the area of the interspinous portion, the conduit permitting engagement of a cord intended to join the prosthesis tightly to at least one of the spinous apophyses.

6. Prosthesis according claim 5, wherein a wall of the interspinous portion which delimits the said conduit is widened at the ends of the conduit in order to eliminate any sharp edge capable of creating a point of wear of the said cord.

7. Prosthesis according to claim 5, further comprising two transverse conduits, each receiving a cord for attaching it to the spinous apophysis of the corresponding vertebra.

8. Prosthesis according to claim 1, wherein said prosthesis is placed in a textile sheath which matches the shape of said prosthesis.

9. Prosthesis according to claim 8, wherein the sheath comprises a small strip sewn onto it on a posterior side of the prosthesis, and intended to serve as an anchoring point for a prosthetic ligament replacing the interspinous and supraspinous ligament.

10. Prosthesis according to claim 1, wherein said lugs are sized in the range of 30 to 40% of the total size of said prosthesis.

11. Prosthesis according to claim 1, wherein a combined length of the two pairs of lugs accounts for 60–90% of the length of the prosthesis.

12. Prosthesis according to claim 1, wherein a combined length of the two pairs of lugs accounts for 66–80% of the length of the prosthesis.

* * * * *